US010098683B2

(12) United States Patent
Vogt (10) Patent No.: US 10,098,683 B2
(45) Date of Patent: Oct. 16, 2018

(54) DEVICE AND METHOD FOR MIXING OF A MULTI-COMPONENT CEMENT (71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 511 days.

(21) Appl. No.: 14/710,847

(22) Filed: May 13, 2015

(65) Prior Publication Data
US 2015/0327904 A1 Nov. 19, 2015

(30) Foreign Application Priority Data
May 15, 2014 (DE) .......................... 10 2014 106 873

(51) Int. Cl.
*A61B 17/88* (2006.01)
*B05C 17/005* (2006.01)
(Continued)

(52) U.S. Cl.
CPC ...... *A61B 17/8833* (2013.01); *A61B 17/8825* (2013.01); *B01F 3/10* (2013.01);
(Continued)

(58) Field of Classification Search
CPC .............................................. A61B 17/8833
See application file for complete search history.

(56) References Cited

U.S. PATENT DOCUMENTS 3,117,696 A * 1/1964 Herman ............ B05C 17/00553
156/500
3,774,816 A 11/1973 Bratton
(Continued)

FOREIGN PATENT DOCUMENTS

CA     1 304 352 A    6/1992
CN     2411061 Y    12/2000
(Continued)

OTHER PUBLICATIONS

Moto, Kikaino, (Principle of Mechanics), Japan, Rikogakusha Publishing Co., Ltd., Jun. 25, 1978, p. 168.
(Continued)

*Primary Examiner* — Abbas Rashid
(74) *Attorney, Agent, or Firm* — Norris McLaughlin & Marcus PA (57) ABSTRACT

A manually drivable device for the mixing of a pasty mixing ware from at least two fluid starting components comprising at least two cartridges having feed plungers; a mixing space to mix the starting components, mixing vanes being provided in the mixing space and mounted such that they can rotate; a lever rotatable about a pivot point operatable manually or a pin that can be shifted in longitudinal direction and operatable manually in order to operate the device; a gear connected to the lever or pin, and connected to the rotatable mixing vanes in the mixing space; and a facility for propelling the feed plungers such that the motion of the lever or pin drives the rotation of the mixing vanes in the mixing space and motion of the feed plungers into the cartridges. The invention also relates to a method for mixing fluid starting components using the device.

22 Claims, 5 Drawing Sheets (51) Int. Cl.
  *B01F 7/00* (2006.01)
  *B01F 13/00* (2006.01)
  *B01F 15/00* (2006.01)
  *B01F 15/02* (2006.01)
  *B05C 17/01* (2006.01)
  *B01F 3/10* (2006.01)

(52) U.S. Cl.
  CPC ........ *B01F 7/0025* (2013.01); *B01F 7/00133* (2013.01); *B01F 7/00141* (2013.01); *B01F 7/00216* (2013.01); *B01F 7/00633* (2013.01); *B01F 13/0027* (2013.01); *B01F 15/00506* (2013.01); *B01F 15/0226* (2013.01); *B01F 15/0237* (2013.01); *B05C 17/00566* (2013.01); *B05C 17/0123* (2013.01); *A61B 2017/8838* (2013.01); *B01F 2215/0029* (2013.01); *B01F 2215/0039* (2013.01)

(56) References Cited

U.S. PATENT DOCUMENTS

| | | | | |
|---|---|---|---|---|
| 3,952,920 | A * | 4/1976 | Bergman | B27G 11/00 222/137 |
| 4,046,288 | A * | 9/1977 | Bergman | B65D 81/325 222/135 |
| 4,234,104 | A * | 11/1980 | Apuzzo, Jr. | B65D 35/285 141/362 |
| 4,240,566 | A * | 12/1980 | Bergman | B05C 17/00516 206/219 |
| 4,973,334 | A * | 11/1990 | Ziemann | A61B 17/8822 606/92 |
| 4,986,443 | A | 1/1991 | Saur et al. | |
| 5,638,997 | A * | 6/1997 | Hawkins | A61B 17/8822 222/327 |
| 5,823,673 | A * | 10/1998 | Muntener | A23G 1/10 366/149 |
| 5,860,739 | A * | 1/1999 | Cannon | B05C 17/00553 222/137 |
| 5,875,928 | A | 3/1999 | Müller et al. | |
| 5,893,488 | A * | 4/1999 | Hoag | A61B 17/8822 222/327 |
| 6,176,396 | B1 * | 1/2001 | Hamada | B05C 17/00553 222/137 |
| 6,702,455 | B2 | 3/2004 | Vendrely et al. | |
| 6,889,872 | B2 * | 5/2005 | Herman | B05C 17/00506 222/137 |
| 7,658,537 | B2 * | 2/2010 | Coffeen | A61B 17/8833 366/139 |
| 8,132,959 | B2 * | 3/2012 | Smit | A61B 17/8833 206/222 |
| 8,357,147 | B2 * | 1/2013 | Burkinshaw | A61B 17/00491 604/181 |
| 8,960,991 | B2 * | 2/2015 | Vogt | B01F 7/00291 366/139 |
| 8,986,313 | B2 | 3/2015 | Vogt et al. | |
| 9,486,298 | B2 * | 11/2016 | Peuker | B05C 17/00553 |
| 9,561,459 | B2 * | 2/2017 | Royce | B01D 46/0067 |
| 2002/0067657 | A1 | 6/2002 | Vendrely et al. | |
| 2008/0144426 | A1 * | 6/2008 | Janssen | B01F 7/00216 366/130 |
| 2009/0105144 | A1 | 4/2009 | Vogt et al. | |
| 2009/0105366 | A1 | 4/2009 | Vogt et al. | |
| 2012/0180529 | A1 * | 7/2012 | Singer | B01F 7/00125 65/135.3 |
| 2013/0138113 | A1 | 5/2013 | Vogt et al. | |

FOREIGN PATENT DOCUMENTS

| | | |
|---|---|---|
| CN | 201959918 U | 9/2011 |
| DE | 33 07 558 A1 | 9/1984 |
| DE | 37 38 960 A1 | 5/1989 |
| DE | 89 07 735 U1 | 10/1989 |
| DE | 195 00 782 A1 | 7/1996 |
| DE | 601 11 605 T2 | 5/2006 |
| DE | 10 2007 052 116 A1 | 4/2009 |
| DE | 10 2007 050 762 B3 | 5/2009 |
| DE | 10 2008 030 312 A1 | 1/2010 |
| DE | 20 2009 017 678 U1 | 4/2010 |
| EP | 2 324 792 A1 | 5/2011 |
| GB | 2 064 664 A | 6/1981 |
| JP | H 02-71868 A | 3/1990 |
| JP | 2013-138845 A | 7/2013 |

OTHER PUBLICATIONS

Notice of Reasons for Rejection issued in corresponding Japanese Application No. 2015-077482 dated Jun. 7, 2016.
German Search Report dated Feb. 6, 2015.
European Search Report dated Oct. 12, 2015.
Moto, Kikaino, (Principle of Mechanics), Japan, Rikogakusha Publishing Co., Ltd., Jun. 25, 1978, p. 168—English Translation provided.
Decision of Rejection issued in corresponding Japanese Application No. 2015-077482 dated Mar. 7, 2017—English translation provided.
Chinese Office Action dated Dec. 27, 2016 and English translation.

* cited by examiner

DEVICE AND METHOD FOR MIXING OF A MULTI-COMPONENT CEMENT

This application claims priority of German Patent Application No. 10 2014 106 873.4, filed May 15, 2014, the disclosure of which is incorporated herein by reference.

DESCRIPTION

The invention relates to a manually drivable device for the mixing of a pasty mixing ware from at least two fluid starting components, in particular for mixing a medical cement, and, if applicable, for storage of the starting components.

The invention also relates to a method for mixing fluid starting components and, if applicable, also for dispensing a mixing ware, in particular for mixing a medical cement.

Specifically, also a subject matter of the invention is a device for storing and mixing polymethylmethacrylate bone cement (PMMA bone cement) that consists, prior to mixing and during storage, of a liquid or pasty first component and separate powdery or pasty second component, as well as a method for mixing the two components, and applying if applicable, the mixed PMMA bone cement and, if applicable, for applying the mixed PMMA bone cement as well as, if desired, an additional pharmaceutical agent that can be admixed or is added to one of the starting components or both starting components.

Polymethylmethacrylate bone cements (PMMA bone cements) have been in use in medicine for decades for permanent mechanical fixation of total joint endoprostheses. These are based on powder-liquid systems, whereby it is customary to use methylmethacrylate as monomer. Recently, polymethylmethacrylate bone cements that are based on the use of cement pastes have been proposed as well (DE 10 2007 050 762 B3, DE 10 2008 030 312 A1, DE 10 2007 052 116 A1). These bone cements have two cement pastes stored separately in suitable cartridges. Cartridges of this type are also often referred to as 2-component cartridges (also as 2K-cartridges). These each contain components of a redox initiator system, aside from at least one monomer and suitable polymers. Said starting components can also be used and applied, preferably, in devices according to the invention and methods according to the invention.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems act in concert. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough, the ingredients of the redox initiator system, previously stored separately in the two pastes, react with each other forming radicals which trigger the radical polymerisation of the at least one monomer. The radical polymerisation then leads to the formation of polymers while consuming the monomer, whereby the cement dough is cured. It is customary to mix the starting components with static mixers, which are attached to the two-component cartridges filled with the starting components for this purpose.

When the two pasty starting components are extruded from the cartridges, the starting components are pushed through a static mixer. As a result, the processes of extruding and mixing proceed concurrently. Mixing the starting components in the static mixer requires a high extrusion force since the pressure drop at the mixing elements in the static mixer is very high. As a result, it is necessary to use powerful pneumatic or mechanical extrusion devices to attain the dispensation and optimal mixing of the pasty starting components. Said pneumatic or mechanical extrusion devices are elaborate from a technical point of view and expensive. An inexpensive option are the manually-operated extrusion guns, which are customary thus far for use with the polymethylmethacrylate bone cements based on powder-liquid systems, which are suitable for said cements, but are not sufficiently powerful for the extrusion and mixing of bone cement pastes by means of static mixers.

If the volumes of the starting components to be mixed are unequal and/or the mixing ratios are very uneven (2:1 and more), very many mixing spirals are required due to the more pronounced volume ratios. The larger the number of mixing spirals needed, the larger is the pressure drop in the static mixer during the mixing process. One pasty component needs to be present, whereas the second component can be either liquid or powdery or pasty as well. The components and/or pastes need to be pressed through the static mixer by a very large force. Due to the nature of manually-operated extrusion devices, the maximally possible extrusion force is limited.

The Semkit® system is time-proven in the adhesives and sealants industry for many years. In this system, a paste is stored in a storage container. A second liquid component is present in a stirring rod, separated from the paste through a valve that is integrated into the stirring rod. Actuating the valve allows the liquid to flow into the paste which can then be mixed by hand.

One disadvantage of a system of this type is that multiple steps are required to get the mixing ware, in particular the medical cement, ready for use. Another disadvantage of the known systems is that simple manual operation of the devices enabling the mixing and dispensation of the pasty masses is not feasible. This is a particularly major disadvantage in the often hectic and stressful operation during a surgical intervention in a patient, i.e. during medical use. Accordingly, it would be desirable to have a device for mixing of the starting components that can be operated more easily and by hand. Since systems operated with compressed air and/or an electric motor require expensive components, the system can no longer be used as a hygienic article for single use.

For pasty polymethylmethacrylate bone cements, solid cartridges of stable shape are required, since the relatively viscous pasty polymethylmethacrylate bone cement dough and/or the pasty starting components can be extruded from storage containers and/or cartridges only through very large extrusion forces. Moreover, it is not feasible to use mixing systems for with bone cements, in which an inadvertent exit of small amounts of paste takes place and in which there is a possibility that air is drawn into the paste. This would not only impair the cleanliness in the operating theatre, but would also mechanically weaken the cement dough through the introduction of air since air bubbles in the cured cement act as fissure initiation sites and thus reduce the stability of the cured bone cement. Therefore, the Semkit® system cannot be used for pasty polymethylmethacrylate bone cements.

Accordingly, it is the object of the invention to overcome the disadvantages of the prior art. Specifically, an inexpensive-to-manufacture and reliably-working device for the mixing of a pasty mixing ware, in particular a medical cement, from at least two fluid starting components and, if applicable, for storage of the starting components, and a method for the mixing of the pasty mixing ware is to be devised, in which the simplest manual operation can be used to mix fluid starting components that are stored separate from each other in cartridges, in particular of highly viscous and/or viscous pastes without having to use an external or additional energy source and without air inclusions arising in the mixing ware.

Specifically, a simple and inexpensive device for the storing and mixing of polymethylmethacrylate bone cement is to be developed that can be used to store at least one starting component in the absence of air, whereby it shall be feasible, through the use of the device, to mix the starting components and preferably to also dispense the cement dough.

The main component of the polymethylmethacrylate bone cement, as mixed ware, shall be a cement paste and the second component can also be pasty or be present in the form of a powder. It shall be possible to store the two starting components of the bone cement separate from each other and to combine them safely by using the device.

The objects of the invention are met by a manually-drivable device for the mixing of a pasty mixing ware from at least two fluid starting components, in particular for the mixing of a medical cement, comprising:

A) at least two cartridges containing the fluid starting components or at least two connectors for at least two cartridges containing the fluid starting components, whereby feed plungers are provided in the cartridges for expelling the starting components from the cartridges;

B) a mixing space for the mixing of the starting components that is connected to the cartridges or connectors for the cartridges such that the starting components are guided into the mixing space when the starting components are expelled from the cartridges by the feed plungers, whereby mixing vanes are provided in the mixing space and are mounted in the mixing space such that they can rotate;

C) a lever that can be rotated about a pivot point and can be operated manually for operation of the device or a pin that can be shifted in longitudinal direction and can be operated manually in order to operate the device;

D) a gear connected to the lever or pin, whereby the gear is appropriately connected to the rotatable mixing vanes in the mixing space such that the mixing vanes can be rotated in the mixing space upon a motion of the lever or pin mediated by the gear; and E) a facility for propelling the feed plungers in the cartridges, appropriately connected to the lever or pin such that the feed plungers can be propelled in the cartridges upon a motion of the lever or pin, such that the motion of the lever or pin drives the rotation of the mixing vanes in the mixing space and the motion of the feed plungers into the cartridges.

Referring to attachable cartridges, it is self-evident that the facility is suitable for propelling the feed plungers in the attached cartridges, whereby the facility is connected to the lever or pin such that the feed plungers can be propelled in the attached cartridges upon a motion of the lever or pin.

In particular and particularly preferably according to the invention, the device is a cementing gun.

According to the invention, the starting components for the mixing ware, in particular for the bone cement, are already present in the cartridges.

It is particularly preferred according to the invention that the device is also well-suited for the storage of the starting components, in particular when the cartridges are inserted into the device or the cartridges are a fixed part of the device.

Conceivable fluid starting components are liquid, pasty, i.e. paste-like, and fluid powdery starting components. At least one of the starting components is pasty or liquid in order to obtain a pasty mixing ware. Preferably, both starting components are pasty.

The mixing ware is particularly preferred to be a bone cement, in particular a PMMA bone cement.

Preferably, the cartridges have one opposite opening in each cartridge provided opposite from the feed plungers for expelling the starting components from the cartridges, whereby the starting components are to be guided through said openings from the cartridges into the mixing space.

It is also preferred for the invention to provide the motion of the lever or pin, by means of which the mixing vanes can be rotated in the mixing space by means of the gear and by means of which the feed plungers are propelled in the cartridges, to be a manually driven motion.

It can also be preferred to arrange on the lever or pin a restoring element, such as a compression spring, by means of which the lever or pin can be returned to its starting position after lever or pin is moved by hand. It is particularly preferable to have the restoring element get tensioned or compressed while the lever and/or pin is moved by hand.

Devices according to the invention can be provided appropriately such that the mixing vanes are inclined consistently with respect to the axis about which the mixing vanes rotate in the mixing space such that the rotation of the mixing vanes in the mixing space causes the mixing ware to be propelled in the mixing space, whereby the mixing vanes are preferred to be inclined with respect to the axis by the same angle.

It is preferred, but not mandatory, to have all mixing vanes be inclined with respect to the axis. In this context, consistently shall be understood to mean that the mixing vanes are inclined by the same angle with respect to the axis about which the mixing vanes rotate. Accordingly, opposite mixing vanes are not arranged to be mirror-symmetrical, but to be rotationally-symmetrical with respect to said axis. The mixing vanes thus form a propeller or a turbine blade configuration.

As a result, the mixing vanes can be used well for both the mixing of the mixing ware and/or the mixing of the two starting components and for propelling the mixing ware in the mixing space. This also enables the use of viscous and/or highly viscous pastes as starting components in the manual force-driven device.

Preferred refinements of the device according to the invention can be characterised in that the gear is force-locking and/or form-fitting.

Gears of this type are particularly well-suited for transmission of the forces exerted by hand. The gear can preferably have little or no play.

A refinement of the present invention proposes the gear to comprise at least one tooth lock washer, at least one friction disk, at least one cogwheel, at least one worm wheel and/or at least one friction wheel by means of which the force and/or torque is transmitted. Preferably, the gear comprises at least one conical tooth lock washer, at least one conical friction disk, at least one conical cogwheel and/or at least one friction wheel for changing the direction of rotation.

Said components can be manufactured easily and inexpensively at the requisite stability even from plastic material. The use of force transmission elements of a conical design is advantageous in that the direction of the transmitted torque can be changed in the gear.

Preferred refinements of the present invention can provide the gear to be a cogwheel gear, a friction wheel gear, a conical wheel gear, a contrate gear, a worm gear or a combination of said gears, preferably additionally comprising a spur gear.

Friction wheel gears are often referred to as friction gear. The gear can be driven either via the front surface of the cogwheel or friction wheel (normal design) or via a lateral surface on the edge of the cogwheel or friction wheel (lateral surface teeth or lateral surface friction). Said gears are easy and inexpensive in design, well-suited for the requisite transmission of force and torque, and not prone to failure in operation.

According to a particularly preferred refinement, the present invention can provide the mixing vanes to be arranged on a rotary shaft (in the mixing space) mounted such as to be rotatable, whereby the rotary shaft extends out of the mixing space, preferably extends out of the mixing space via a seal, and the rotary shaft is connected to the gear such that the rotary shaft with the mixing vanes can be rotated in the mixing space by means of a motion of the lever or pin.

This is advantageous in that, firstly, the design is particularly simple, and, additionally, the central axis of the mixing space is filled by the rotary shaft such that no poorly mixed parts of the mixing ware can be pressed through in this location.

Moreover, the invention can preferably provide a clutch in the connection of the gear to the mixing vanes, in particular in the rotary shaft mounted such as to be rotatable, or in the gear, whereby the clutch allows the mixing vanes to rotate in one direction of rotation and prevents or reduces rotation in the opposite direction of rotation.

As a result, the mixing vanes rotate in one direction only or mainly in one direction. If the mixing vanes are also utilised to propel the mixing ware, this prevents the mixing vanes from rotating in reverse direction during the reverse motion of the lever or pin and thus from inadvertently conveying the mixing ware back in the direction of the cartridges.

In this context, the invention can provide a free-wheel clutch on or in the gear or provide a sprung rotating clutch in the connection from the gear to the mixing vanes, in particular in the rotary shaft mounted such as to be rotatable.

Sprung rotating clutches of this type, which are presently also referred to as free-wheel clutches, are known, for example, from ballpoint pens and can be manufactured very inexpensively, while their function is sufficient for the application according to the invention. In sprung rotating clutches of this type, a serrated circular surface engages a matching counterpart, whereby the two circular surfaces are pressed onto each other by means of an elastic spring. The serration has a steep flank in one direction of rotation, preferably a perpendicular flank, and a shallow flank in the other direction of motion. When the driven circular surface rotates in the direction of the steep flank, the other circular surface rotates along, since the steep flanks engage each other. Upon a rotation in the reverse direction, the shallow flanks slide over each other and the other circular surface does not rotate along due to slip. As a result, the rotation of the shaft is transmitted to the mixing vanes in one direction only.

As a result, what this attains, in easy and inexpensive manner, is that the mixing vanes rotate in one direction only and cannot rotate in the opposite direction upon restoration or reverse motion of the lever or pin and cannot inadvertently push the mixing ware in the mixing space in the direction of the cartridges.

According to the invention, the facility for propelling the feed plungers in the cartridges can be a mechanical propelling facility. This makes the design of the device simple.

A refinement of the present invention proposes that the facility for propelling the feed plungers in the cartridges is a clamp rod having a tiltable jamming opening or a gear rack having a unidirectionally-acting snap-in locking means, whereby the jamming opening or the snap-in locking means is connected to the lever or the jamming opening or the snap-in locking means is connected to the pin, in particular the jamming opening or the snap-in locking means is connected to the pin via a lever.

The facility for propelling the feed plungers in the cartridges can also be designed to include a spindle. As a result of the measures specified above, the feed plungers can be propelled step-by-step by multiple operation and/or multiple strokes of the lever or pin. As a result, even major quantities of the mixing ware can be mixed by hand from viscous or highly viscous pastes such as is required, for example, in the case of bone cements. Jamming openings of this type are known, for example, from cartridge guns for silicone.

In order to enable extended storage of the starting components in the device, the invention can provide at least one manually-opening valve element or manually-opening closures to be arranged in the connection between the mixing space and the cartridges or in the connectors for the cartridges.

As a result, the facility can also be used well for storage of the starting components since the starting components in the cartridges are closed off by the cartridge walls versus the outside, on one side by the feed plungers, and on the opposite side by the closures or the valve element. As a result, the content stays sterile and does not dry out so readily during storage.

It is preferred to use, as valve element, an axially rotatable cylindrical tube section that touches against the cylindrical internal walls of the mixing space, whereby two bushings are arranged in the jacket surface of the tube section, whereby the bushings can be made to overlap with the connections to the cartridges by rotating the tube section. The overlapping of the bushings and connections to the cartridges causes the valve element to be open. When the bushings are made to overlap with connection openings to the cartridges, the valve element is in an opened position. Said design is simple and inexpensive to manufacture from plastics and its operation is not error-prone. It is particularly preferred to have an operating lever fastened to the tube section and the operating lever to extend through an opening in the wall of the mixing space, in particular through a radial slit in the wall of the mixing space. As a result, the tube section can be manually rotated in the mixing space and can thus be opened and, if desired, closed again.

A device according to the invention that is particularly easy to operate can be attained in that the device comprises a handle for holding the device by one hand, whereby the lever or the pin or an operating element for manual operation of the lever or pin is arranged appropriately in the region of the handle such that the lever or the pin or operating element can be operated by the same hand that holds the device by the handle.

As a result, the device can be operated by one hand. This simplifies manual operation.

Preferred devices according to the invention can be characterised in that the mixing space comprises a dispensing opening for application of the mixing ware on the side opposite from the connection to the cartridges, whereby it is preferred to have an application tube connected or be connectable to the dispensing opening.

As a result, the mixing ware can be applied and/or dispensed and used directly by the device.

A refinement of the present invention also proposes static shearing elements for mixing of the mixing ware to be arranged in the mixing space, whereby it is preferred that said shearing elements cut the flow of the mixing ware through the mixing space and/or that the shearing elements are arranged in axial direction relative to the axis about which the mixing vanes rotate, between the mixing vanes.

The use of shearing elements cutting through the mixing ware in the feeding direction attains more vigorous mixing of the mixing ware.

A refinement of the invention also proposes a circular arc or circular arc section to be arranged on said lever and to have on its front face or its side surface a driving row of cogs or a friction surface arranged by means of which a cogwheel or friction wheel of the gear can be driven or that a serration or a friction surface is arranged on the pin by means of which a cogwheel or friction wheel of the gear can be driven.

The driving row of cogs or friction surface can also be inclined with respect to the front face or side surface of the circular arc or circular arc section. In addition or alternatively, the gear wheel or friction wheel of the gear driven by the row of cogs or friction surface can be a bevel gear wheel.

Due to the use of a circular arc with the lever, the tilting motion of the lever can be directly converted into a rotational motion of the circular arc by means of which the gear is being driven. Said design is inexpensive to implement and simple and not malfunction-prone.

Particularly advantageous refinements of the invention can be characterised in that the gear comprises an appropriate transmission ratio such that, upon a full motion of the lever or pin, the mixing vanes perform at least 2 turns in the mixing space, preferably perform between 2 and 10 turns in the mixing space, particularly preferably between 2.5 and 5 turns in the mixing space.

If said transmission ratios are selected, one stroke is sufficient for sufficient mixing and sufficient propulsion of the mixing ware in the mixing space even in the case of highly viscous and very viscous pastes as starting components without the manual force of a normal user no longer being enough to operate the device manually, in particular by one hand.

Moreover, the invention can provide the facility for propelling the feed plungers in the cartridges to be appropriately connected to the lever or pin such that, upon a full motion of the lever or pin, the feed plungers are propelled in the cartridges by at least 1 mm, preferably are propelled in the cartridges by between 2 mm and 12 mm, particularly preferably are propelled in the cartridges by between 5 mm and 7 mm.

At this level of propulsion, which preferably is selected to match the rotating speed of the mixing vanes in the mixing space, the starting components can still be dispensed from the cartridges even in the case of viscous and/or highly viscous starting components.

Particularly preferred embodiments of the invention can provide the facility for propelling the feed plungers in the cartridges to be appropriately connected to the lever or pin such that the feed plungers expel at least 90% of the starting components from the cartridges upon 5 to 25 full motions of the lever or pin, preferably such that the feed plungers expel at least 90% of the starting components from the cartridges upon 10 to 20 full motions of the lever or pin.

As a result, the device is very useful, in particular, for mixing and applying bone cement. The motion cycles as specified can be performed without too much effort without fatigue to the arm and/or hand of the user, but also in a manner such that each individual motion, i.e. each individual stroke of the lever or pin, does not require too much force.

The device is preferred to consist of plastics, particularly preferably of thermoplastics, with the exception of restoring elements and/or spring elements. It is even more particularly preferred to have the restoring elements and/or spring elements also consist of plastics.

According to the invention, the device is encased by a housing such that reaching into parts of the device that move during its application, other than the lever or pin, is prevented. The lever or pin are being operated in order to use the device and must therefore be accessible to the user.

The underlying objects of the invention are also met by a method for the mixing of fluid starting components and, if applicable, also for the dispensation of a pasty mixing ware, in particular for the mixing of a medical cement, preferably by means of a device as described herein, characterised in that A) a lever is being tilted or a pin is being moved in longitudinal direction;

B) the force of the motion of the lever or pin propels feed plungers in at least two cartridges and presses the starting components contained in the cartridges into a mixing space by means of the feed plungers; and C) the force of the motion of the lever or pin rotates mixing vanes in the mixing space, whereby the transmission of the force of the lever or pin for rotation of the mixing vanes is effected by means of a gear.

In this context, the invention can provide the rotation of the mixing vanes in the mixing space to mix the starting components in the mixing space and convey them in the direction of a dispensing opening.

Due to said concurrent mixing and dispensation, even highly viscous and viscous pastes can be used as starting components for the mixing ware. Concurrently, manual operation of the device and/or manual driving of the lever or pin is still sufficient to drive the mixing vanes and the feed plungers in the device.

A refinement of the invention also proposes that the lever or pin, after being moved, is restored to the starting position by a restoring element, whereby it is preferred that the feed plungers are not moved and the mixing vanes are not rotated during said restoration to the starting position.

As a result, the device can be used by multiple strokes of the lever or pin, which allows the force to be applied and the amount of mixing ware produced per stroke to be adjusted and/or smaller portions to be used.

The invention can just as well provide the gear to be driven by means of a sprocket wheel or friction sprocket wheel on the lever or a row of cogs or a friction surface on the pin.

The invention also proposes to repeat the motion of the pin or lever, preferably between 5 and 25 times, in order to empty the cartridges by at least 90%. It is particularly preferred to repeat the motion of the pin or lever 10 to 15 times, in order to empty the cartridges by at least 90%.

The invention can just as well provide the gear to transmit a full stroke of the lever or pin into at least 2 turns of the mixing vanes in the mixing space, preferably into 2.5 to 5 turns of the mixing vanes in the mixing space.

The invention can provide for the cartridges to be opened towards the mixing space, preferably by manual operation of a valve element, prior to the first operation of the lever or pin. This allows the starting components to be stored previously in the cartridges for longer periods of time.

The invention is based on the surprising finding that, due to the manually-operated lever or pin being connected to both the rotatable mixing vanes and to the facility for propelling the feed plungers in the cartridges, it is feasible to have one stroke of the lever or pin or preferably multiple strokes of the lever or pin extrude the starting components from the cartridges and concurrently mix the starting components actively. With the mixing vanes in a suitable position, by the mixing vanes being inclined with respect to the axis about which the mixing vanes rotate, and with the direction of rotation of the mixing vanes being appropriate, the rotation of the mixing vanes provides for additional propulsion of the mixing ware in the mixing space and finally expels the mixing ware from a dispensing opening.

Preferably, fixed shearing elements are arranged perpendicular to the conveying direction of the mixing ware in the way of blades between the rotating regions of the mixing vanes. When the mixing vanes are driven in the mixing space via a central rotary shaft, the shearing elements can be used, additionally, for mounting and positioning the rotary shaft in the mixing space. A central rotary shaft is preferred, since it prevents parts of the mixing ware that are not mixed or poorly mixed in the axial centre of the mixing space from being conveyed to the dispensing opening and thus from being dispensed from the device.

In order to render the minor rotation (the small angle of rotation) of the lever and/or the minor linear stroke of the pin usable for strong mixing by means of the mixing vanes, it has been evident in the scope of the invention that a gear can be used in order to transmit the minor motion of the lever or pin into a larger number of turns and a higher angular velocity of the mixing vanes.

But still, and this is in the spirit of the invention, a single stroke of the lever or pin cannot and shall not be sufficient to fully empty the cartridges. For this reason, it is necessary, during the restoration of the lever or pin, which is preferably attained, according to the invention, using a restoring element such as a spring, to prevent the feed plungers from being retracted and to prevent the mixing vanes from rotating in the reverse direction and thus pushing the mixing ware back in the direction of the cartridges. According to the invention, a free-wheel clutch or any other device for attaining or forcing a preferential direction of rotation is used for the directional rotation of the mixing vanes and is arranged in the connection between the lever or pin and the mixing vanes. In order to prevent a reverse motion of the feed plungers or facility for driving the feed plungers, a gear rack having a unidirectionally-acting snap-in locking means is used, such as are used, for example, in a car lifting jack, or a clamping device is used by means of which a clamp rod is clamped by tilting the clamping device and propelled in one direction, while the clamping device detaches from the rod upon a reverse motion and thus cannot move the rod in the reverse direction. Said clamping devices are known for cartridge guns, such as cartridge skeleton guns.

Driving the starting components in and out of the cartridges and concurrently driving the mixing ware in the mixing space by means of a gear allows even very viscous and highly viscous pasty cements and cement components to still be extruded and mixed by hand. In the device according to the invention and the method according to the invention, the energy for mixing of the starting components no longer needs to be derived from the force of the propulsion of the starting components out of the cartridges. Rather, the mixing ware is mixed by the active motion of the mixing vanes and, preferably, is propelled by the mixing vanes being in a suitable position. The force for mixing therefore no longer needs to be derived from the hydrostatic pressure of the starting components, but rather is transferred directly in the mixing space from the mixing vanes to the mixing ware.

Due to the presence of the gear, the minor stroke of the lever or pin can be used to enable strong mixing and strong propulsion by means of a relatively rapid rotation of the mixing vanes.

A preferred manually-operable device according to the invention is well-suited for the storage and mixing of starting components of a medical cement, in particular of a PMMA bone cement, and, moreover, is well-suited for application of the mixed medical cement and can, for example, be designed to have multiple cartridges (preferably two cartridges) with a cylindrical internal space, whereby each cartridge has a cylindrical feed plunger arranged in it that closes the internal space of the cartridge and is axially mobile, by means of which the starting components can be expelled from the internal space of the cartridge. In this context, the starting components are guided into a mixing space through an opening that is situated opposite from the feed plungers. In this location, the starting components are mixed and propelled by rotating mixing vanes. Finally, the mixed mixing ware is expelled in the front through a dispensing opening or, preferably, through an application tube or dispensing tube, and applied. A lever arranged in the region of a pistol handle is used to operate the device. The device is arranged in a housing that is enclosed except for the dispensing opening or the connector for the dispensing tube and except for a bushing for the lever. The lever is connected to a clamping device for unidirectional propulsion of a rod. The rod is connected to a yoke by means of which the feed plungers are propelled in the cartridges. The yoke is either long enough to still reach the rear-side walls of the cartridges when the feed plungers are propelled fully in the direction of the openings to the mixing space, or the yoke comprises cutting edges that cut through the walls of the cartridges when the feed plungers are being propelled. The clamping device engages the rod when the lever is manually pulled towards the pistol handle by closing the hand, which also holds the pistol handle, and moves the rod with the yoke and thus the feed plungers into the cartridges, which pushes the starting components into the mixing space. If the lever was returned into the starting position by a restoring element, which was tensioned when the lever was pressed, the clamping device detaches and is moved against the rod such that the rod and the yoke can no longer be moved backwards and detach from the feed plungers.

The same motion of the lever also rotates a sprocket that is arranged to be concentric about the pivot of the lever. The cogs of the sprocket are engaged by a first small gear wheel, whose rotary shaft is connected to a larger gear wheel that has a larger diameter and more cogs than the small gear wheel. The friction cogwheels can be implemented by conical cogwheels or crown gears in order to change the direction of rotation of the drive shaft of the mixing vanes with respect to the direction of rotation of the lever. A free-wheel clutch and/or a sprung rotating clutch is arranged in the drive shaft that forms the rotary shaft of the mixing vanes. Said clutch will be able to be moved in one direction only on the side of the rotary shaft facing the mixing vanes such that the mixing vanes can be moved in the mixing space in one direction only. In this context, the mixing vanes are inclined appropriately with respect to the rotary shaft in the mixing space such that the mixing ware in the mixing space is driven in the direction of the dispensing opening.

Frictions wheels can be used just as well as an alternative to the embodiment comprising cogwheels.

The polymethylmethacrylate bone cements that are preferred to be used as mixing ware in devices and methods according to the invention particularly preferably use methylmethacrylate as monomer and thus use a powder or a paste containing methylmethacrylate as a first starting component. Matching redox initiator systems usually consist of peroxides, accelerators and, if applicable, suitable reducing agents, which, according to the invention, are present in the second starting component. Radicals are formed only if all ingredients of the redox initiator systems act in concert. For this reason, the starting components of the redox initiator system are arranged appropriately in the cement pastes, which are separated by the spatially separated cartridges, such that they cannot trigger a radical polymerisation. The separation is attained by the valve element or the closures or any other separating device that can be opened, by means of which the starting components can be separated reliably. The starting components are thus stable during storage provided the composition and the selection of the cartridge material are appropriate. Only when the starting components are mixed to produce a cement dough as mixing ware, the ingredients of the redox initiator system, previously stored separately in the two starting components, react with each other forming radicals which trigger the radical polymerisation of the at least one monomer. The radical polymerisation then leads to the formation of polymers while consuming the monomer, whereby the cement dough is cured (in particular after application of the cement dough). A dynamic mixer, i.e. mixing vanes rotating in the mixing space, are used to mix the starting components and to propel the cement dough.

BRIEF DESCRIPTION OF THE DRAWINGS

Further exemplary embodiments of the invention shall be illustrated in the following on the basis of five schematic figures, though without limiting the scope of the invention. In the figures.

Identical or similar components are identified in the figures, to some extent, through the same reference numbers even if different cementing guns are concerned.

Figure 1:
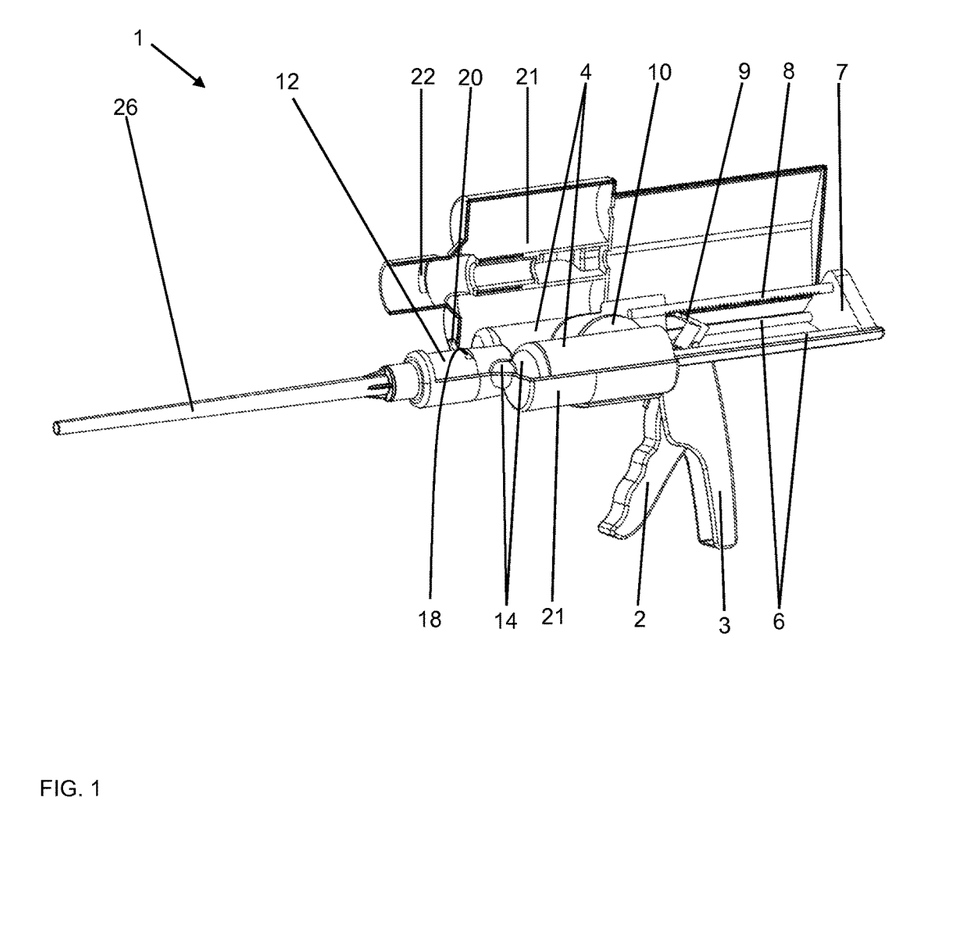
FIG. 1: shows a schematic perspective view of a device according to the invention folded open.

FIG. 1 shows a schematic perspective view of a device 1 according to the invention that is opened towards the top. The device 1 comprises a lever 2 that can be pulled and is arranged in front of a pistol handle 3. As a result, the device 1 can be held in one hand and the lever 2 can be operated with the same hand that pulls and/or operates the lever 2. The lever 2 is supported like in a bearing with respect to the handle 3 such that it can rotate about an axis, whereby an elastic compression spring (not shown) is arranged between lever 2 and handle 3 such that the compression spring can always return the lever 3 to the starting position shown. The lever 2 comprises three depressions for fingers to be placed in such that it can be comfortably operated by the fingers of the same hand that also holds the handle 3.

Two cylindrical cartridges 4 are arranged side-by-side inside the device 1 and contain the starting components (not shown) that are used to produce the mixing ware. Moreover, feed plungers (not shown in FIG. 1) are arranged on the rear side in the cartridges 4 (on the right in FIG. 1) and can be shifted in longitudinal direction. The feed plungers are connected, on their rear side (on the right in FIG. 1), to two rods 6 or the rods 6 touch against the rear side of the feed plungers. The rods 6 are connected to each other through a yoke 7. The purpose of the rods 6 is to push the feed plungers in the cartridges 4 to the front end of the cartridges 4 (on the left in FIG. 1) without the yoke touching against the rear-side opening of the cartridges 4 and thus preventing a further motion of the rods 6 into the inside of the cartridges 4 and thus a further motion of the feed plungers in the direction of the front side of the cartridges 4 (on the left in FIG. 1).

Moreover, the yoke 7 is connected to a gear rack 8, whereby the cogs of the gear rack 8 comprise a steep flank (in the direction of the front side—on the left in FIG. 1) and a shallow flank (in the direction of the rear side—on the right in FIG. 1). Alternatively, the yoke 7 can just as well be formed by a blade that connects the rods 6 to the gear rack 8 and cut through the walls of the cartridges 4 when the yoke 7 and the feed plungers are being driven towards the front. Said design is advantageous in that the device 1 can be designed more compact, since the rods 6 can then be made significantly shorter, whereby the gear rack 8, in its starting position, then is arranged further in the direction of the front side of the device 1, but it is a disadvantage that a larger mechanical force needs to be exerted in order to have the blades of the yoke cut through the walls of the cartridges 4. Moreover, blades of this type cannot be manufactured from plastics. Therefore, the design shown, having the wide yoke 7, is preferred.

The cogs of the gear rack 8 are engaged by a snap-in locking means 9 that is connected, in mobile manner, to the lever 2 by means of a shaft and that is mounted elastically sprung against the cogs of the gear rack 8. The snap-in locking means 9 engages, by its front edge, the steep flanks of the cogs of the gear rack 8 when the lever 2 is rotated and/or tilted by moving the lever in the direction of the handle 3, since the shaft about which the lever 2 is rotated is situated below the connection to the snap-in locking means 9. Accordingly, the upper part of the lever 2 tilts in the opposite direction from the lower part of the lever 2, by which the lever is being held.

As a result, the gear rack 8 is driven towards the front (to the left in FIG. 1) and, by means of the gear rack 8, the yoke 7 and the rods 6 and thus the feed plungers in the cartridges 4 are driven towards the front such that the starting components are expelled from the cartridges 4 towards the front. When the lever 2 is released or no pressure or insufficient pressure is exerted any longer on the lever 2 by the hand of the user, the spring mechanism of the lever 2 ensures that the snap-in locking means 9 moves in the direction of the rear side of the device 1. Concurrently, the snap-in locking means 9 is tilted against the lever 2 and slips over the shallow flanks of the cogs of the gear rack 8 such that the gear rack 8 is not being moved in the direction of the rear side of the device 1 (on the right in FIG. 1).

Due to said spring mechanism of the snap-in locking means 9, the next pressing or pulling of the lever 2 towards the handle 3 causes the snap-in locking means 9 to engage cogs in the gear rack 8 that are arranged further back (further on the right in FIG. 1). As a result, each stroke of the lever 2 can push the gear rack 8 and thus the rods 6 and the feed plungers a few cogs and/or cog lengths further down in the direction of the front side of the device 1.

The lever 2 is connected, additionally, to a sprocket wheel 10 that is also rotated along when the lever 2 is rotated. Cogs are arranged on a side surface of the sprocket wheel 10 and engage the cogwheels of a gear (not shown in FIG. 1). Said gear drives mixing vanes (not shown in FIG. 1) that can rotate on a rotary shaft (not shown in FIG. 1) in a mixing space 12. The mixing space 12 is connected to the internal space of the cartridges 4 by means of a connection 14 such that, upon propulsion of the feed plungers, the starting components are guided from the cartridges 4 via the connection 14 into the mixing space 12.

The rotation of the mixing vanes mixes the starting components in the mixing space 12 and conveys them in the direction of a dispensing tube 16 on the front side of the device 1 and finally expels them through the dispensing tube 16. Using a free-wheel clutch (not shown in FIG. 1), the mixing vanes can rotate in the mixing space 12 in one direction and/or in one direction of rotation only. Accordingly, the mixing vanes do not rotate along with the motion of the lever 2 towards the starting position that is attained by the compression spring between the lever 2 and the handle 3. The gear having a suitable transmission ratio, the mixing vanes rotate two to five times about the rotary shaft upon a full stroke of the lever 2. Exemplary designs of the gear and device for free-wheeling, and/or of the free-wheel clutch are described in FIGS. 2 to 4, which also explain their mode of working in more detail.

Initially, the cartridges 4 are closed by a valve element 18 that is arranged, such that it can be rotated, as a tube section, in which the part of the mixing space 12 facing the connection 14 is arranged. The valve element 18 comprises two openings (not shown) that can be made to overlap with the openings of the connection 14. For this purpose, the valve element 18 can be rotated by means of a valve lever 20. The valve lever 20 extends through a gap in the wall of the mixing space 12.

The entire assembly is arranged in a housing 21 and is manufactured from plastics. The spring elements and compression springs can just as well be manufactured from metal. An upper part of the housing 21 is shown in FIG. 1 to be folded open towards the top in order to afford a view into the inside of the device 1. The valve lever 20 of the valve element 18 projects through a slit 22 in the housing 21. In operation, the housing 21 is closed and all moving parts are thus covered. In order to get the device 1 and/or the cementing pistol 1 ready, the valve lever 20 is rotated first and thus the cartridges 4 are being opened towards the mixing space 12. Subsequently, the lever 2 is operated (pressed) repeatedly and the starting components of the cement in the cartridges 4 are thus being pressed into the mixing space 12 where they are mixed. Due to the pressure from the cartridges 4 and by means of the propulsion by the mixing vanes in the mixing space 12, the cement mixture is mixed and expelled towards the front through the dispensing tube 16 and can be applied in this location.

Figure 2:
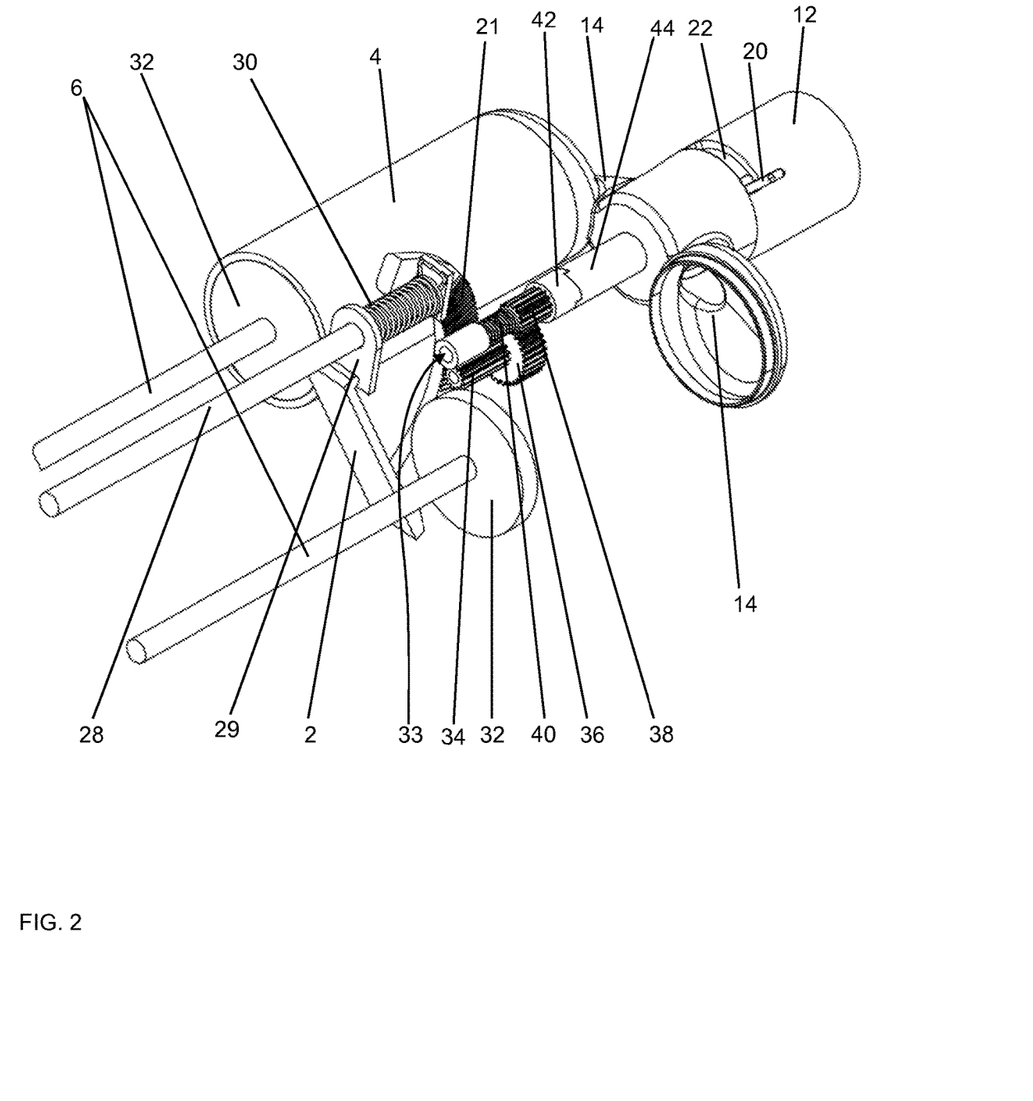
FIG. 2: shows a schematic perspective partial view of a device according to the invention.

FIG. 2 shows a schematic perspective partial view of a device according to the invention. The device 1 is shown without its housing in FIG. 2 and the detail focuses on the essential parts of the drive of the device. The device comprises two cartridges 4 arranged such as to be parallel to each other, of which only one is drawn in FIG. 2. The second cartridge has not been drawn to afford a better view of the gear. The device resembles the one according to FIG. 1, whereby the present design uses, instead of the gear rack, a simple smooth cylindrical clamp rod 28 that is engaged by a tiltable jamming disc 29 having a jamming opening, instead of by the snap-in locking means. Accordingly, the jamming disc 29 comprises a jamming opening arranged in the centre through which extends the clamp rod 28, whereby the internal diameter of the jamming opening is larger than the external diameter of the clamp rod 28 such that the jamming disc 29 can be inclined on the clamp rod 28 and thus the jamming opening can jam with the clamp rod 29. Clamp rods 28 of this type in cementing pistols and cementing skeleton pistols are known.

The jamming disc 29 is connected to a lever 2 such that it can be tilted about an axis and/or rotated, whereby the lever 2 can be rotated manually on the underside (not shown). A spring 30 transfers the jamming disc 29 into a sliding (not jammed) position when the lever 2 is not being operated. When the lever 2 is moved, i.e. when the part of the lever 2 shown in FIG. 2 is moved towards the front (towards the right top in FIG. 2), the jamming disc 29 jams with the clamp rod 28. As a result, the clamp rod 28 is pushed towards the front (towards the right top in FIG. 2).

The clamp rod 28 is connected by means of a yoke (not shown) to two rods 6 of which only one rod 6 is shown in FIG. 2. Accordingly, when the clamp rod 28 is moved towards the front, the rod 6 also moves towards the front and pushes two feed plungers 32 into the cartridges 4, which are arranged in parallel, which causes the content of the cartridges 4 to be pressed towards the front out of the cartridges 4 into a connection 14 and from there into a mixing space 12.

A sprocket wheel 10 is fastened to the lever 2 and rotates when the lever 2 is rotated. A rotary shaft 33 is arranged in the mixing space 12, mounted such that it can rotate, and has mixing vanes (not shown in FIG. 2) arranged on it that can rotate about the rotary shaft 33 in the mixing space 12. The rotary shaft 33 can be driven by the sprocket wheel 10 by means of a gear. The sprocket wheel 10 is engaged by a first small cogwheel 34 of the gear that is connected, by a shaft, to a second larger cogwheel 36 of the gear. The second larger cogwheel 36 finally engages a third small cogwheel 38 that is fastened to the rotary shaft 33. As a result of said transmission, the rotary shaft 33 rotates approximately three times about its own axis upon a full stroke of the lever 2 and thus upon a rotation of the sprocket wheel 10 by approx. 45°. The mixing vanes rotate accordingly in the mixing space 12.

A free-wheel clutch and/or a sprung rotating clutch is arranged in the rotary shaft 33 between the third cogwheel 38 and the mixing space 12. The spring mechanism 40 for this purpose can be seen on the rotary shaft 33. The free-wheel clutch and/or the sprung rotating clutch is implemented through two interlocked circular discs 42, 44 engaging each other that are pushed onto each other by the spring mechanism 40. Flanks of the cogs of the circular discs 42, 44 differing in slope depending on the direction of rotation, attain a preferential direction of the rotation of the part of the rotary shaft 33 that extends into the inside of the mixing space 12.

The openings of the connection 14 to the mixing space 12 can be closed and opened by means of a valve element analogous to the one according to FIG. 1. The valve element can be rotated in a slit 22, and thus can be opened and closed, through a valve lever 20. The working mechanism of the device according to FIG. 2 is the same as the working mechanism of the device 1 according to FIG. 1. Upon each stroke of the lever 2, the feed plungers 32 are propelled further into the inside of the cartridges 4. Concurrently, the same motion of the lever 2 rotates the rotary shaft 33 and thus rotates the mixing vanes in the mixing space 12. Due to the rotation of the mixing vanes, the content of the mixing space 12 is being mixed and extruded through an exit opening (not shown in FIG. 2) out of the device.

Figure 3:
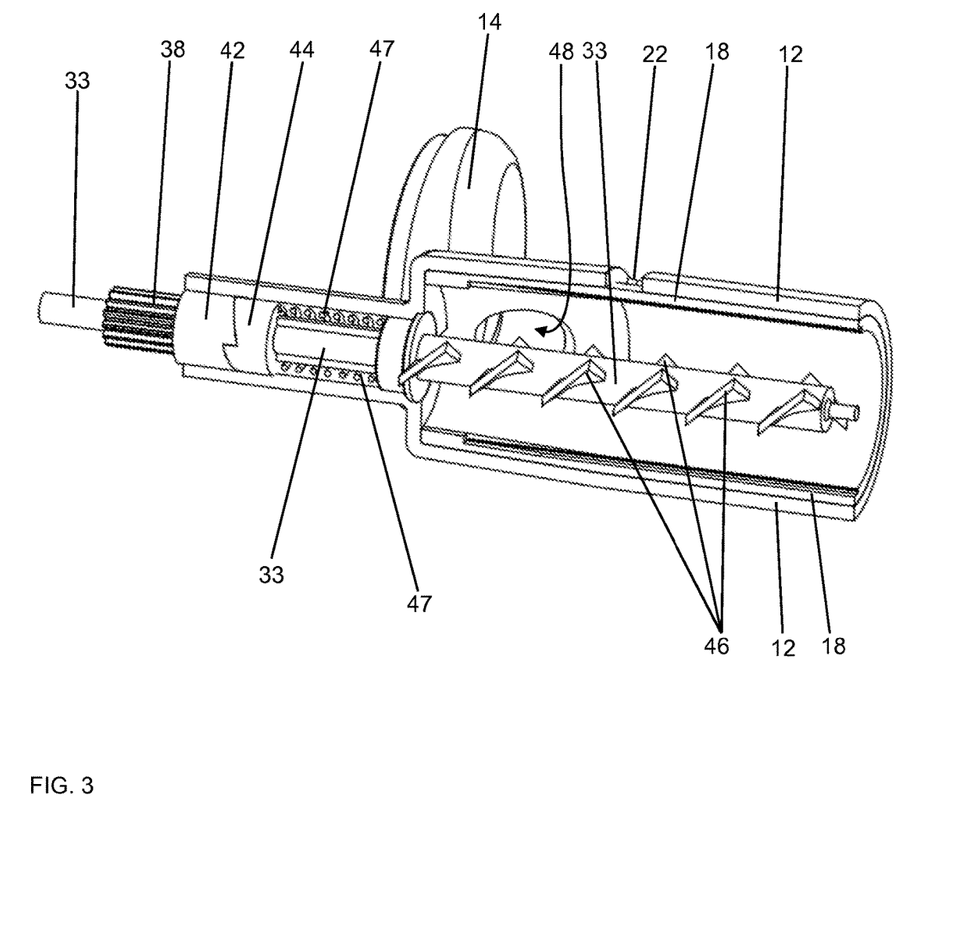
FIG. 3: shows a schematic perspective partially sectioned view of a device according to the invention.

FIG. 3 shows a schematic perspective and partially sectioned view of the device according to the invention according to FIG. 2, in which the two mutually-engaging, interlocked circular discs 42, 44 of the free-wheel clutch and/or sprung rotary clutch and the mixing vanes 46 can be seen well. Moreover, it can be seen through the section made how the valve element 18 rests in and/or touches against the walls of the mixing space 12. A spring 47 pushes the right (front) circular disc 44 onto the left (rear) circular disc 42. The mixing vanes 46 are arranged inclined on the rotary shaft 33 in the same sense of orientation with respect to the rotary shaft 33 such that a rotation of the rotary shaft 33 propels the mixing ware in the mixing space 12 (towards the right in FIG. 3).

When the upper edge of the (third) cogwheel 38 rotates into the image plane, the friction of the shallow flanks of the circular discs 42, 44 is insufficient for the right circular disc 44 to rotate along with the left circular disc 42. The circular discs 42, 44 slip over each other and the rotary shaft 33 arranged in the mixing space 12 does not rotate along.

When the lower edge of the (third) cogwheel 38 rotates into the image plane, the steep (perpendicular) flanks of the circular discs 42, 44 engage each other such that the right circular disc 44 rotates along with the left circular disc 42. The rotary shaft 33 arranged in the mixing space 12 rotates along with the mixing vanes 46. Accordingly, a repeated motion of the lever 2 and thus of the gear-mediated rotary motion of the rotary shaft 33 in front of the mixing space 12 results just in an unidirectional rotation of the rotary shaft 33 in the mixing space 12 and thus of the mixing vanes 46. Accordingly, the mixing vanes 46 always drive the mixing ware in the mixing space 12 towards the dispensing opening (on the right in FIG. 3).

The valve element 18 comprises a round valve opening 48 in the form of a passage through the wall of the tube-shaped valve element 18. The valve opening 48 rotates along with the valve element 18. When the valve element 18 is rotated into an appropriate position, as shown in FIG. 3, the valve opening 48 overlaps with the access to the connection 14 and/or to the cartridge connector 14. A second valve opening (not shown) then establishes an opening to the connection 14 of the second cartridge (not shown in FIG. 3). As a result, the two cartridges are opened towards the mixing space 12 and the starting components can be conveyed from the cartridges into the mixing space 12.

According to another embodiment of the invention that can be considered to be a variant of the design according to FIG. 3, the invention can provide the third cogwheel 38 and the left circular disc 42 to comprise a cylindrical bushing, and the rotary shaft 33 to extend through these bushings such that the third cogwheel 38 and the left circular disc 42 are arranged on the rotary shaft 33 such that they can be shifted along the symmetry axis of the rotary shaft 33. The rotary shaft 33 is then formed in the direction of the yoke as a spindle having a thread. An internal thread is provided in the yoke in the form of a screw nut by means of which the rods and thus the feed plungers are propelled such that the yoke and thus the rods and the feed plungers are pulled in the direction of the connections 14 of the cartridges to the mixing space 12 by the rotation of the spindle. Moreover, the third cogwheel 38 and the left circular disc 42 are spring-mounted in the direction of the right circular disc 44 by a compression spring between the thread of the spindle and the third cogwheel 38. The third cogwheel 38 and the left circular disc 42 are preferably provided as a single part. For this purpose, the third cogwheel 38 preferably has a larger height than the drive cogwheel (the second cogwheel) engaging the third cogwheel 38 such that the third cogwheel 38 can glide on the drive cogwheel without the full height of the cogwheel no longer being usable any more. For this purpose, it is sufficient if the third cogwheel 38 is higher than the drive cogwheel by the height of the cogs of the circular discs 42, 44. As a result of said design, the rotating rotary shaft 33 of the mixing vanes 46 can also be used as drive spindle for propulsion of the feed plungers.

Figure 4:
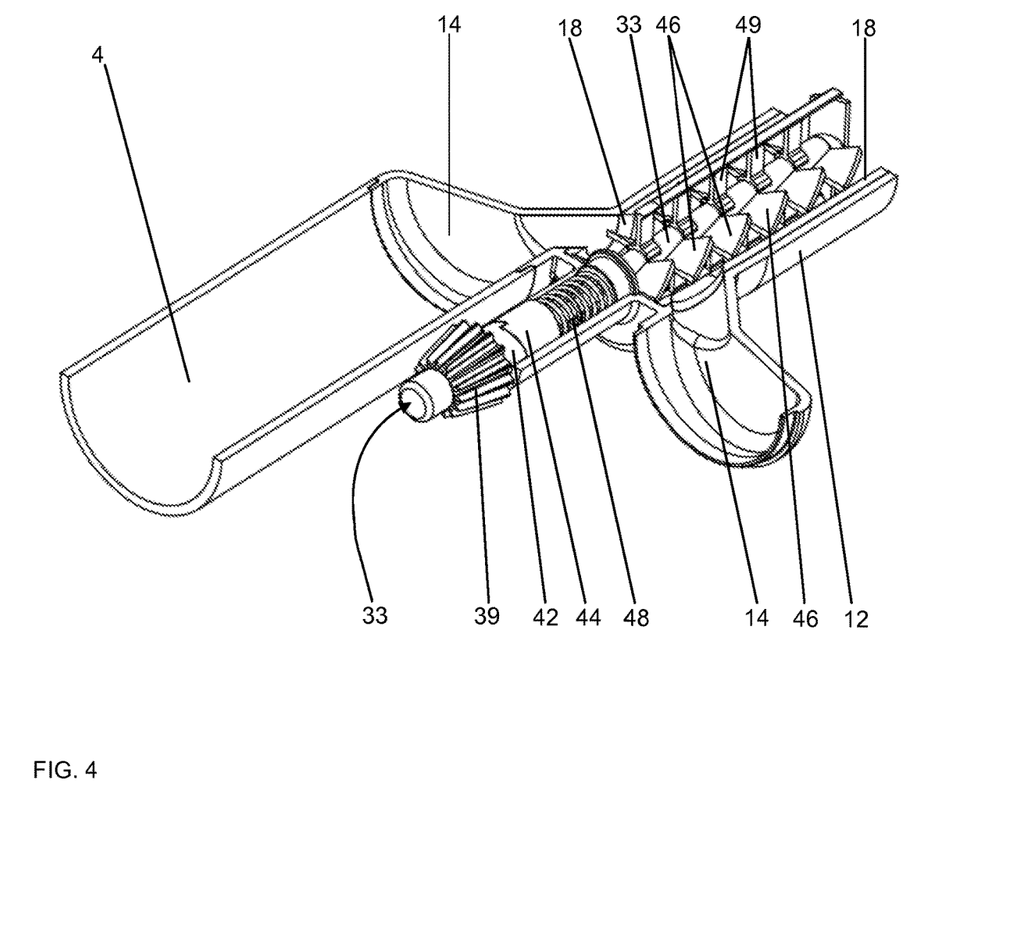
FIG. 4: shows another schematic perspective partially sectioned view of a device according to the invention.

FIG. 4 shows another schematic perspective and partially sectioned view of a device according to the invention. The design is identical to the one according to FIGS. 2 and 3, whereby a conical cogwheel 39 instead of the usual cogwheels is incorporated such that the direction of rotation can be reversed by the gear. As a result, the cogs of the sprocket wheel (not shown in FIG. 4) can just as well be arranged on the front side of the sprocket wheel. For this purpose, the other cogwheels, in part or all of them, are also provided as conical cogwheels (not shown). Preferably, the sprocket wheel also comprises an inclined surface and thus forms a conical sprocket wheel.

Static shearing elements 49 that do not rotate along with the rotary shaft 33 are arranged in the mixing space 12. The purpose of said shearing elements 49 is to cut the mixing ware, which is being propelled towards the front (to the right top back in FIG. 4) perpendicular to the conveying direction and to thus improve the mixing. A series of five shearing elements not shown in FIG. 4 is arranged with mirror symmetry on the opposite side of the rotary shaft 33 in the mixing space 12. As a result, the rotary shaft 33 is supported as in a bearing in the mixing space 12 by the shearing elements 49, which end in cylindrical shell segments.

The purpose of the spring mechanism 47 is to push the right (front) circular disc 44 onto the left (rear) circular disc 42. When the upper edge of the conical cogwheel 39 rotates in counter-clockwise direction with respect to the rotary shaft 33 (viewed from the back—viewed from left bottom front in FIG. 4), the friction of the shallow flanks of the circular discs 42, 44 is insufficient for the right circular disc 44 to move along with the left circular disc 42. Rather, the circular discs 42, 44 slip over each other and the part of the rotary shaft 33 arranged in the mixing space 12 and the mixing vanes 46 do not rotate.

When the conical cogwheel 39 rotates in clockwise direction (viewed from left bottom front in FIG. 4), the steep (perpendicular) flanks of the circular discs 42, 44 engage each other such that the right circular disc 44 rotates along with the left circular disc 42. The rotary shaft 33 arranged in the mixing space 12 rotates along with the mixing vanes 46. Accordingly, the repeated motion of the lever 2 and thus the repeated gear-mediated rotary motion of the rotary shaft 33 in front of the mixing space 12 result(s) just in a unidirectional rotation of the rotary shaft 33, and thus of the mixing vanes 46, in the mixing space 12. Accordingly, the mixing vanes 46 always drive the mixing ware in the mixing space 12 towards the dispensing opening.

Figure 5:
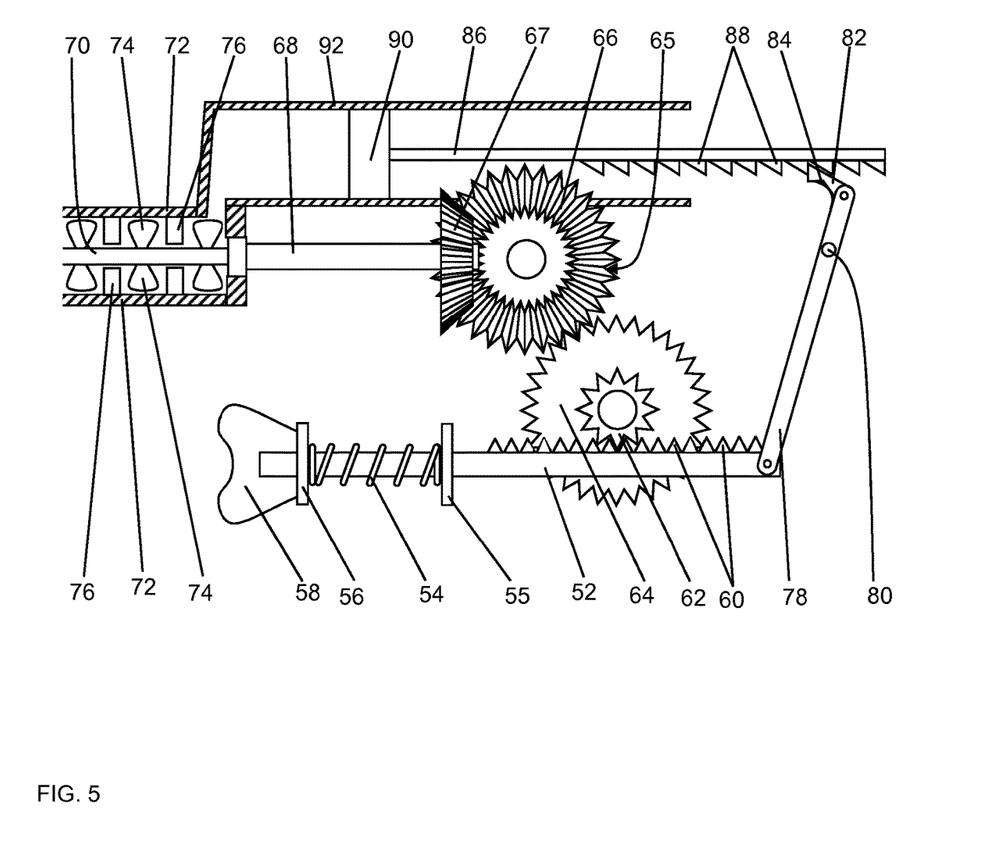
FIG. 5: shows a schematic side view of a part of another device according to the invention.

FIG. 5 shows a schematic side view of a functionally essential part of a further device according to the invention and/or a cementing gun according to the invention. This device also is shown in the absence of a housing. A part of the device is shown sectioned in the depiction of FIG. 5. Sectioned surfaces are shown hatched in FIG. 5.

The device is operated by means of a spring-mounted pin 52 that is mobile in longitudinal direction, instead of a lever.

The spring mechanism is attained by means of a spring 54 that is fastened between a bracket 55 on the housing (not shown) and a bracket 56 on a button 58 or a key 58. When the button 58 is pushed in the direction of the bracket 55, the compression spring 54 is being compressed and takes up energy. Releasing the pressure, the pin 52 is pushed to the front again (to the left in FIG. 5) by the button 58.

In the rear region arranged inside the housing, cogs 60 are arranged on one side on the pin 52 such that the pin 52 forms a gear rack 52 in this region. Said gear rack 52 is arranged to be axially mobile with respect to a cogwheel 62 such that the cogs 60 of the gear rack 52 and/or pin 52 engage the cogs of the cogwheel 62. The cogwheel 62 is connected by means of its shaft to a free-wheel clutch 64 that ends in an outer sprocket wheel. The free-wheel clutch 64 rotates the outer sprocket wheel with the cogwheel 62 only if the cogwheel 62 rotates in clockwise direction with respect to the direction of view of the observer of FIG. 5, i.e. when the pin 52 is pushed towards the back (to the right in FIG. 5). Free-wheel clutches 64 of this type are known, for example, from bicycles, but can be designed very simply for the present purpose, since they do not need to have particularly easy-running idling properties.

The outer sprocket wheel of the free-wheel clutch 64 engages a cogwheel 65 that is arranged on a cogwheel shaft such that it can rotate. A conical cogwheel 66 is arranged on said cogwheel shaft and rotates along with the cogwheel 65. The conical cogwheel 66 is arranged in front of the cogwheel 65, with respect to the viewing plane, in FIG. 5. A second conical cogwheel 67, arranged orthogonally, engages the conical cogwheel 66 and drives a rotary shaft 68, 70. Accordingly, the rotary shafts of the conical cogwheels 66, 67 are perpendicular to each other. The inclination of the cone jacket surface of the conical cogwheels 66, 67 is inclined at an angle of 45° with respect to the rotary shaft thereof.

The second conical cogwheel 67 is arranged on the rear rotary shaft 68. The front rotary shaft 70 is arranged in a mixing space 72 that is bordered by mixing space walls 72 and is shown in cross-section in FIG. 5. For this purpose, the rotary shaft 68, 70 is guided through a seal into the mixing space 72, in which the rotary shaft 68, 70 is supported as in a bearing such that it can rotate. Mixing vanes 74 are arranged on the front rotary shaft 70 and rotate in the mixing space 72 when the rotary shaft 68, 70 rotates. The mixing vanes 74 are inclined appropriately with respect to the plane perpendicular to the rotary shaft 70 such that the mixing vanes 74 drive a mixing ware in the mixing space 72 (to the left in FIG. 5) towards the front, when the rotary shaft 70 is driven by the pin 52 being pressed and/or by a motion of the pin 52 to the right in FIG. 5.

To improve the mixing of the mixing ware, perpendicular shearing elements 76 are arranged in the mixing space 72 and extend as rectangular discs perpendicularly from the mixing space wall 72 in the direction of the rotary shaft 70. The shearing elements 76 cut through the cement paste (the mixing ware) that is being driven in the direction of a front dispensing opening (not shown in FIG. 5).

The pin 52 is connected on its rear side to a lever 78 by means of a rotatable shaft. The lever 78 is supported as in a bearing by a shaft 80 such that it can be rotated and/or tilted with respect to the housing. The lever 78 can be designed in telescoping manner in order to be able to move along on the linear motion of the pin 52. A snap-in locking element 82 is connected to the lever 78 on the opposite side of the lever 78 by means of a shaft such that it can rotate. The snap-in locking element 82 is pressed, by a leaf spring 84, against a rod 86 bearing cogs 88.

The cogs 88 of the rod 86 have a perpendicular flank, which points to the right in FIG. 5, and a shallow flank, which points to the left in FIG. 5. The snap-in locking element 82 engages the perpendicular flanks of the cogs 88 and glides over the shallow flanks of the cogs 88. As a result, upon a motion of the pin 52 in the direction of the rear side of the device (to the right in FIG. 5), the rod 86 is pushed in the direction of the front side of the device (to the left in FIG. 5) by the lever 78 and the snap-in locking element 82.

The rod 86 pushes onto a feed plunger 90 that is arranged in a cartridge 92 that is filled with one of the starting components for the mixing ware and/or with the bone cement, and that is connected to the mixing space 72. The rod 86 can just as well be fastened to the feed plunger 90. A second cartridge (not shown) is situated right before or behind the cartridge 92 shown in cross-section in FIG. 5, and is arranged to be parallel to the first cartridge 92 and has a linearly mobile feed plunger (not shown) arranged in it. The design of the two parallel cartridges 92 is identical in this context. The rod 86 is shaped in the way of a yoke such that the feed plunger of the front (second cartridge) is also driven by the rod 86. The front cartridge also exits into the mixing space 72.

Due to the propulsion of the rod 86 and the feed plungers taking place in separate pushes, the components are conveyed out of the cartridges 92 into the mixing space 72 and are mixed therein by means of the static shearing elements 76 and the rotating mixing vanes 74, and are driven to the front by the rotating mixing vanes 74. Lastly, the ready-mixed mixing ware (the medical cement) is expelled to the front out of the device and applied.

It is preferred according to the invention to have at least one closure (not shown) that can be opened manually or one valve element (not shown) that can be opened manually arranged on the openings or in the openings between the cartridges 92 and the mixing space 72, by means of which the mixing space 72 is separated from the two cartridges 92. The closure and/or the valve element, as the case may be, closes the content of the cartridges 92 off from the outside and renders the device well-suited for storage of the starting components (or of the cartridge contents, as the case may be).

Instead of cogwheels and conical cogwheels, friction wheels and conical friction wheels can be used just as well in all embodiments.

The features of the invention disclosed in the preceding description and in the claims, figures, and exemplary embodiments, can be essential for the implementation of the various embodiments of the invention both alone and in any combination.

LIST OF REFERENCE NUMBERS

1 Device/cementing gun
2 Lever
3 Handle/pistol handle
4 Cartridge
6 Rod
7 Yoke
8 Gear rack
9 Snap-in locking means
10 Sprocket wheel
12 Mixing space
14 Connection/cartridge connector 16 Dispensing tube
18 Valve element
20 Valve lever
21 Housing
22 Slit
28 Rod
29 Jamming rod
30, 47 Spring
32 Feed plunger
33 Rotary shaft
34, 36, 38 Cogwheel
39 Conical cogwheel
40 Spring mechanism
42, 44 Circular disc
46 Mixing vanes
48 Valve opening
49 Shearing element
52 Pin/gear rack
54 Spring
55, 56 Bracket
58 Button/key
60, 88 Cog
62 Cogwheel
64 Free-wheel clutch
65 Cogwheel
66, 67 Conical cogwheel
68 Rear rotary shaft
70 Front rotary shaft
72 Mixing space wall
74 Mixing vanes
76 Shearing element
78 Lever
80 Shaft
82 Snap-in element
84 Leaf spring
86 Rod
90 Feed plunger
92 Cartridge

The invention claimed is:

1. A manually drivable device for mixing of a pasty mixing ware from at least two fluid starting components, said device comprising:
   at least two cartridges containing the fluid starting components or at least two connectors for at least two cartridges containing the fluid starting components, whereby feed plungers are provided in the cartridges for expelling the starting components from the cartridges;
   a mixing space for the mixing of the starting components that is connected to the cartridges or connectors for the cartridges such that the starting components are guided into the mixing space when the starting components are expelled from the cartridges by the feed plungers, whereby mixing vanes are provided in the mixing space and are mounted in the mixing space such that they can rotate;
   a lever that can be rotated about a pivot point and can be operated manually for operation of the device or a pin that can be shifted in the longitudinal direction and can be operated manually in order to operate the device;
   a gear connected to the lever or pin, whereby the gear is appropriately connected to the rotatable mixing vanes in the mixing space such that the mixing vanes can be rotated in the mixing space upon a motion of the lever or pin mediated by the gear, wherein a clutch is provided in the connection of the gear to the mixing vanes, whereby the clutch allows the mixing vanes to rotate in one direction of rotation and prevents or reduces rotation in the opposite direction of rotation; and
   a facility for propelling the feed plungers in the cartridges, appropriately connected to the lever or pin such that the feed plungers can be propelled in the cartridges upon a motion of the lever or pin, such that the motion of the lever or pin drives the rotation of the mixing vanes in the mixing space and the motion of the feed plungers into the cartridges.

2. The device according to claim 1, wherein
the mixing vanes are inclined consistently with respect to the axis about which the mixing vanes rotate in the mixing space such that the rotation of the mixing vanes in the mixing space causes the mixing ware to be propelled in the mixing space.

3. The device according to claim 1, wherein
the gear is force-locking and/or form-fitting.

4. The device according to claim 1, wherein
the gear comprises at least one tooth lock washer, at least one friction disk, at least one cogwheel, at least one worm wheel and/or at least one friction wheel by means of which force and/or torque is transmitted.

5. The device according to claim 1, wherein
the gear is a cogwheel gear, a friction wheel gear, a conical wheel gear, a contrate gear, a worm gear or a combination of said gears.

6. The device according to claim 1, wherein
the mixing vanes are arranged on a rotary shaft that is mounted such as to be rotatable, whereby the rotary shaft extends out of the mixing space, and the rotary shaft is connected to the gear such that the rotary shaft with the mixing vanes can be rotated in the mixing space by means of a motion of the lever or pin.

7. The device according to claim 6, wherein
the clutch is provided in the rotary shaft.

8. The device according to claim 1, wherein the clutch is a sprung rotating clutch provided in the connection from the gear to the mixing vanes.

9. The device according to claim 1, wherein
the facility for propelling the feed plungers in the cartridges is a clamp rod having a tiltable jamming opening or a gear rack having a unidirectionally-acting snap-in locking means, whereby the jamming opening or the snap-in locking means is connected to the lever or the jamming opening or the snap-in locking means is connected to the pin.

10. The device according to claim 1, wherein
at least one manually-opening valve element or manually-opening closures is/are arranged in the connection between the mixing space and the cartridges or in the connectors for the cartridges.

11. The device according to claim 1, wherein
the device comprises a handle for holding the device by one hand, whereby the lever or the pin or an operating element for manual operation of the lever or pin is arranged appropriately in the region of the handle such that the lever or pin or operating element can be operated by the same hand that holds the device by the handle.

12. The device according to claim 1, wherein
the mixing space comprises a dispensing opening for application of the mixing ware on a side opposite from the connection to the cartridges.

13. The device according to claim 1, wherein
static shearing elements for mixing of the mixing ware are arranged in the mixing space.

14. The device according to claim 1, wherein
a circular arc or circular arc section is arranged on the lever and has on its front face or its side surface a driving row of cogs or a friction surface arranged by means of which a cogwheel or friction wheel of the gear can be driven or in that a serration or a friction surface is arranged on the pin by means of which a cogwheel or friction wheel of the gear can be driven.

15. The device according to claim 1, wherein
the gear comprises an appropriate transmission ratio such that, upon a full motion of the lever or pin, the mixing vanes perform at least 2 turns in the mixing space.

16. The device according to claim 1, wherein
the facility for propelling the feed plungers in the cartridges is appropriately connected to the lever or pin such that, upon a full motion of the lever or pin, the feed plungers are propelled in the cartridges by at least 1 mm.

17. The device according to claim 1, wherein
the facility for propelling the feed plungers in the cartridges is appropriately connected to the lever or pin such that the feed plungers expel at least 90% of the starting components from the cartridges upon 5 to 25 full motions of the lever or pin.

18. A method for the mixing of fluid starting components, said method being carried out with the device according to claim 1, said method comprising:
tilting the lever or moving the pin of said device in the longitudinal direction;
a force produced by tilting the lever or moving the pin propelling the feed plungers in the at least two cartridges and pressing the starting components contained in the cartridges into the mixing space by means of the feed plungers; and
the force produced by tilting the lever or moving the pin rotating the mixing vanes in the mixing space, whereby the transmission of the force of the lever or pin for rotating of the mixing vanes is effected by means of the gear wherein the lever or pin, after being moved, is restored to a starting position by a restoring element, whereby the feed plungers are not moved and the mixing vanes are not rotated during said restoration to the starting position.

19. The method according to claim 18, wherein
the rotating of the mixing vanes in the mixing space mixes the starting components in the mixing space and conveys them in the direction of a dispensing opening.

20. The method according to claim 18, wherein
the gear is driven by means of a sprocket wheel or friction sprocket wheel on the lever or a row of cogs or a friction surface on the pin.

21. The method according to claim 18, wherein
the motion of the pin or lever is repeated in order to empty the cartridges by at least 90%.

22. The method according to claim 18, wherein
the gear transmits a full stroke of the lever or pin into at least 2 turns of the mixing vanes in the mixing space.

* * * * *